US005602140A

United States Patent [19]
Isobe et al.

[11] Patent Number: 5,602,140
[45] Date of Patent: Feb. 11, 1997

[54] PURINE DERIVATIVES AND SUPPRESSANTS FOR INFLAMMATORY DISEASES

[75] Inventors: Yoshiaki Isobe; Nobuyoshi Chiba; Yuso Goto; Hideharu Sato, all of Toda, Japan

[73] Assignee: Japan Energy Corporation, Tokyo, Japan

[21] Appl. No.: 410,838

[22] Filed: Mar. 27, 1995

[30] Foreign Application Priority Data

Mar. 28, 1994 [JP] Japan .................. 6-081000
Mar. 7, 1995 [JP] Japan .................. 7-074651
Mar. 8, 1995 [JP] Japan .................. 7-077394

[51] Int. Cl.$^6$ .................. A61K 31/52; C07D 473/30; C07D 233/90
[52] U.S. Cl. .................. 514/262; 544/265; 548/326.5
[58] Field of Search .................. 544/265; 514/262

[56] References Cited

U.S. PATENT DOCUMENTS

| | | | |
|---|---|---|---|
| 4,578,460 | 3/1986 | Francia | 544/49 |
| 4,728,644 | 3/1988 | Imayoshi et al. | 514/212 |
| 4,772,606 | 9/1988 | Sircar et al. | 514/262 |
| 4,885,301 | 12/1989 | Coates | 514/263 |
| 4,975,467 | 12/1990 | Ku et al. | 514/712 |
| 5,073,559 | 12/1991 | Coates | 514/262 |
| 5,098,906 | 3/1992 | Sircar et al. | 514/262 |
| 5,250,534 | 10/1993 | Bell et al. | 514/258 |
| 5,270,465 | 12/1993 | Ferrand et al. | 544/258 |
| 5,272,153 | 12/1993 | Mandell et al. | 514/263 |

FOREIGN PATENT DOCUMENTS

| | | |
|---|---|---|
| 292660 | 11/1988 | European Pat. Off. . |
| 293063 | 11/1988 | European Pat. Off. . |
| 352960 | 1/1990 | European Pat. Off. . |
| 0442204A2 | 12/1990 | European Pat. Off. . |
| 94/00453 | 1/1994 | WIPO . |

OTHER PUBLICATIONS

Ohsaki, Chem. Pharm. Bull. 34, 36 (1986).
Broughton et al. (1975), "Antiallergic Acivity of 2–Phenyl–8–Asapurin–6–Ones," 18 *J. Med. Chem.* 11:1117–1122.

Iizuka, K. et al. "Highly Selective Inhibitors of Thromboxane Synthetase!. Imidazole Derivatives" J. Med. Chem., vol. 24, No. 10, pp. 1139–1148, 1981.

Morita, K. et al. "Ozagrel Hydrochloride Monohydrate, a Thromboxane Synthase Inhibitor, and Its Metabolites of Hepatic Microsomal Drug Metabolism" Chem. Pharm. Bull, vol. 7, No. 12, pp. 3351–3354, Dec. 1989.

*Primary Examiner*—Mark L. Berch
*Attorney, Agent, or Firm*—Testa, Hurwitz & Thibeault, LLP

[57] ABSTRACT

Purine derivatives shown by general formula [I] or pharmacologically acceptable salts thereof. Suppressants for inflammatory diseases containing an effective ingredient of said purine derivative.

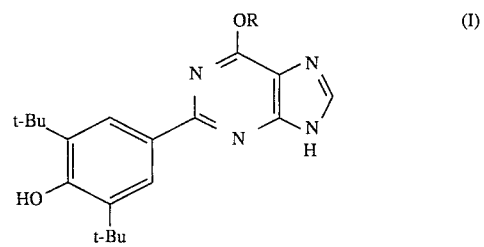

(wherein, R represents one group selected from the groups composed of H atom, a straight chain alkyl group having 1–10 carbon atoms, a branched chain alkyl group having 3–10 carbon atoms, an alkyl group having 1–10 carbon atoms substituted with one carboxyl group, 4-carboxybenzyl group and phenethyl group).

Above mentioned purine derivatives prevent the tissue damages due to mediators such as active oxygen and $TXA_2$ in the initial stage of inflammation, and prevent the subsequent aggravation of inflammatory responses due to the adhesion of activated leukocytes to the cells in the lesion, and exhibit efficacy as anti-inflammatory drugs in all stages of inflammatory diseases caused by leukocytes.

5 Claims, No Drawings

5,602,140

PURINE DERIVATIVES AND SUPPRESSANTS FOR INFLAMMATORY DISEASES

FIELD OF THE INVENTION

This invention relates to novel purine derivatives and pharmaceutical compositions containing thereof. The pharmaceutical compositions containing novel purine derivatives of the present invention are useful as suppressants for inflammatory diseases (anti-inflammatory drugs), particularly for allergic diseases such as asthma and dermatitis, pulmonary diseases such as adult respiratory distress syndrome (ARDS) and autoimmune diseases such as nephritis and rheumatism. The compositions are also useful as suppressants for inflammatory diseases (anti-inflammatory drugs) due to inflammation caused by leukocytes in the lesion.

BACKGROUND OF THE INVENTION

Inflammation is a series of biological defensive responses caused by extrinsic irritative stimulation due to invasion of foreign materials (or bodies) into the body. In the above-mentioned series of biological defensive responses, the major responses include the increase of vascular permeability and infiltration of inflammatory cells, mainly of leukocytes. Autoimmune responses accompanied by intrinsic stimulation also induce inflammatory responses in addition to extrinsic stimulation due to allergenic substances (antigen) and bacteria. These inflammations induced by immune responses have been reported to cause inflammatory diseases through complicated processes. For example, inflammatory diseases of respiratory organs such as asthma and bronchitis are said to occur through two stages (see Medical Immunology, 15, 61–71 (1988)). That is, the first stage is a release of chemical mediators such as histamine and $TXA_2$ from activated mast cell by extrinsic stimulation to result in the constriction of bronchial muscle. This first stage generally occurs within 30 minutes after the inhalation of antigens (exogenous stimulation) and is called immediate type asthma. The second stage is an invasion of eosinophiles (one type of leukocytes) into the lesion of bronchus followed by swelling of bronchial mucosa in the lesion by active oxygen produced by the eosinophile and results in the inflammation. This second stage occurs 8–16 hours after inhalation of antigens and is called delayed type asthma. Such inflammatory responses occurring by leukocytes are considered to make asthma intractable.

Heretofore, various drugs having specific antagonistic activity to chemical mediators such as histamine or $TXA_2$ released from mast cell in the above-mentioned first stage have practically been used. These drugs are to be effective to ameliorate the symptoms in the first stage but insufficiently active to suppress the inflammation of the second stage, because various chemical mediators interact in the first stage and mere suppression of one specific factor (chemical mediator) among various ones can not sufficiently inhibit the progress into the second stage. Furthermore, these drugs have insufficient inhibitory effect against inflammation mainly due to leukocytes in the second stage. Thus, drugs which are antagonistic to various chemical mediators not only in the first stage, but also effective for suppression of inflammatory responses caused by leukocytes in the second stage have been desired.

In the other inflammatory diseases, leukocytes activated by stimulus have been reported to be a major cause of inflammatory responses. In pulmonary diseases such as adult respiratory distress syndrome (ARDS), leukocytes (neutrophils) are activated by endotoxin secreted from bacteria and play major role in inflammatory responses. The activated neutrophils adhere to pulmonary capillary vessels, and neutrophils release active oxygen and protease, damage capillary vessels and result in inflammation (see. Journal of Clinical and Experimental Medicine (IGAKU NO AYUMI), Special issue, Pulmonary Diseases, p. 437 (1991) pub. by Ishiyaku Publishers, Inc., Tokyo, Japan). In addition, arachidonic acid metabolites, such as $TXA_2$, and LTs, such leukotriene $B_4$, PAF and so on accelerate the tissue damages of vascular cells by neutrophils and exacerbate the inflammatory response. Autoimmune diseases caused by immunological mechanism accompanied by intrinsic stimulus, for example nephritis, are mainly caused by activated leukocytes (neutrophils). It is said that tissue damages caused by mediators such as active oxygen and $TXA_2$ which are released from activated neutrophils result in nephritis when the neutrophils attack immune complex composed of antigen (glomerular basement membrane) and autoantibody to this. Many patients are suffering from various inflammatory diseases caused by inflammatory responses due to leukocytes, thus novel compounds useful for the treatment of inflammatory diseases and suppressants containing said novel compounds active against inflammatory diseases have been desired. Particularly, drugs which exhibit excellent suppressive effect for inflammatory responses due to leukocytes and inhibit the adhesion of leukocytes to the cells in the lesion have been desired.

The inventors of the present invention have been investigating novel compounds effective for inflammatory diseases and accomplished the present invention. That is, the present inventors synthesized novel compounds of purine derivatives shown by the general formula [I] below, evaluated their biological activities and found them to be effective for the suppression of inflammatory diseases and accomplished the present invention.

SUMMARY OF THE INVENTION

Therefore, the object o f the present invention is to provide novel compounds exhibiting pharmacological activities useful for the suppression of inflammatory diseases and suppressants for inflammatory diseases containing said novel compounds. The present invention, particularly provides novel purine derivatives exhibiting pharmacological activities useful for the suppression of inflammatory diseases and suppressants for inflammatory diseases containing said novel purine derivatives.

The purine derivatives of the present invention include compounds represented by the following general formula [I]

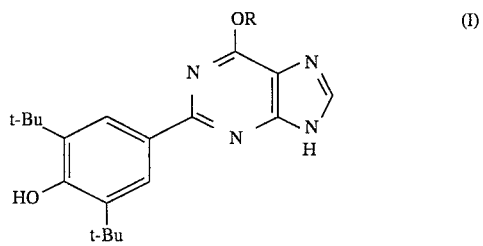

(wherein, R represents one group selected from the groups composed of H atom, a straight chain alkyl group having 1–10 carbon atoms, a branched chain alkyl group having 3-10 carbon atoms, an alkyl group having 1-10 carbon atoms substituted with one carboxyl group, 4-carboxybenzyl group and phenethyl group)
and pharmacologically acceptable salts thereof.

DETAILED DESCRIPTION OF THE INVENTION AND PREFERRED EMBODIMENT

The suppressants for inflammatory diseases of the present invention include pharmaceutical compositions containing an effective ingredient of novel purine derivative represented by the above-mentioned general formula [I]. Particularly, the suppressants for inflammatory diseases of the present invention include suppressants for any one of inflammatory diseases caused by leukocytes and asthma accompanied with bronchial constriction, adult respiratory distress syndrome (ARDS), nephritis, and autoimmune diseases.

Preferred examples of pharmacologically acceptable salts of said compounds of the present invention are pharmacologically acceptable hydrochloride, sulfate, acetate, hydrobromide, phosphate, succinate, maleate, fumarate, citrate, gluconate, methanesulfonate, p-toluenesulfonate, and salts containing pharmacologically acceptable cation for example sodium salt, potassium salt, and calcium salt. The pharmacologically acceptable salts of said purine derivatives can be prepared by mixing said purine derivatives with a corresponding acid or a base containing the corresponding cation, followed by purification such as recrystallization.

Purine derivatives of the present invention shown by general formula [I] can be practically exemplified in compounds in which R represents an alkyl group such as
2-(3,5-di-tert-butyl-4-hydroxyphenyl)-6-methoxypurine,
2-(3,5-di-tert-butyl-4-hydroxyphenyl)-6-n-propoxypurine,
6-n-butoxy-2-(3,5-di-tert-butyl-4-hydroxyphenyl)purine,
2-(3,5-di-tert-butyl-4-hydroxyphenyl)-6-n-hexyloxypurine,
2-(3,5-di-tert-butyl-4-hydroxyphenyl)-6-n-octyloxypurine,
in which R represents an alkyl group substituted with one carboxyl group such as 6-(3-carboxy-n-propoxy)-2-(3,5-di-tert-butyl-4-hydroxyphenyl)purine, 6-(5-carboxy-n-pentyloxy)-2-(3,5-di-tert-butyl-4-hydroxyphenyl)purine, 6-(7-carboxy-n-heptyloxy)-2-(3,5-di-tert-butyl-4-hydroxyphenyl)purine, and 2-(3,5-di-tert-butyl-4-hydroxyphenyl)-6-phenethyloxypurine, 6-(4-carboxybenzyloxy)-2-(3,5-di-tert-butyl-4-hydroxyphenyl)purine and 2-(3,5-di-tert-butyl-4-hydroxyphenyl)-6-hydroxypurine. These compounds were evaluated in the Test Examples shown later in the scavenging of active oxygen or prevention of lipid peroxidation. Among these exemplified compounds shown by general formula [I], five compounds shown above in which R represents an alkyl group and those compounds in which R represents phenethyl group are preferred compounds. Particularly, two compounds in which R represents n-propyl or n-butyl are more preferable compounds. Furthermore, three compounds shown by general formula [I] in which R represents ethyl, pentyl or heptyl group exhibit closely similar biological activities and are deemed preferred compounds in addition to above-mentioned 5 compounds in which R represents alkyl group.

The purine derivatives of the present invention can be prepared by the following processes 1-5 (Scheme I) to give an intermediate, 2-(3,5-di-tert-butyl-4-methoxymethyloxyphenyl)-9-benzyl-6-hydroxypurine (Formula VII), followed by processes 6-8 (Scheme II) introducing a substituent R at position-6 of the purine structure. The outline of processes 1-5 is shown below.

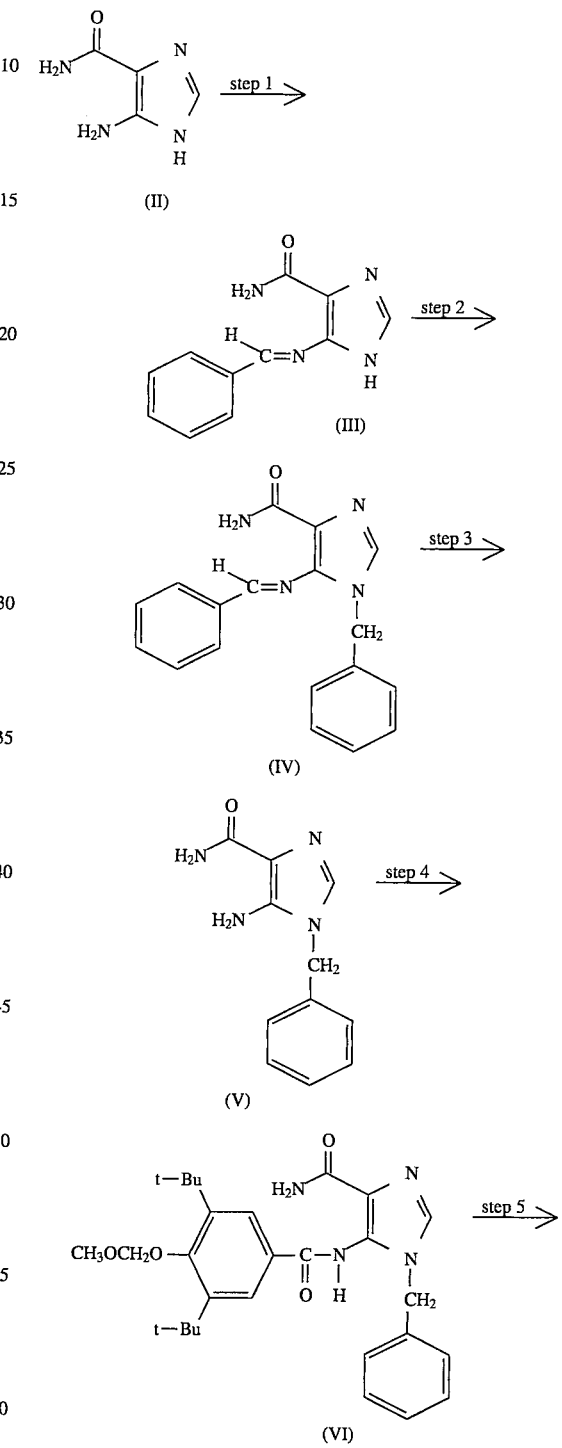

-continued
Scheme I

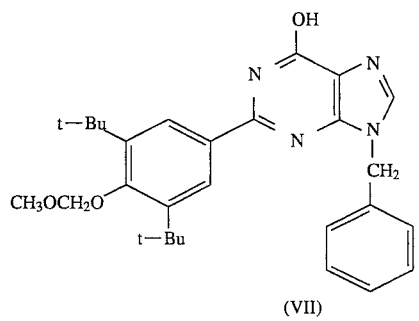

(VII)

Process 1

Raw materials of 4-amino-5-imidazolecarboxamide (Formula II) and benzaldehyde are reacted preferably in the presence of a base and at temperatures of 0°–100° C. in a solvent which dissolves both compounds or solventless condition to give a compound (Formula III). As a base, preferably nitrogen compounds without having active hydrogen, more suitably such as triethylamine or pyridine, can be used and said compound (Formula III) can be obtained quantitatively from 4-amino-5-imidazolecarboxamide.

Process 2

The compound (Formula obtained by the process 1 and benzyl chloride are caused to react preferably in the presence of a base and at temperatures of 0°–100° C. in a solvent which dissolves both compounds or solventless condition to give a compound (Formula IV). As a base, preferably nitrogen compound without having active hydrogen, more suitably such as triethylamine or pyridine, can be used and said compound (Formula IV) can be obtained quantitatively from said material (Formula III).

Process 3

The compound (Formula IV) obtained by the process 2 is treated with an acid to give compound (Formula V). As an acid, preferably hydroacid, more suitably such as hydrochloric acid or sulfuric acid, can be used and said compound (Formula V) can be obtained quantitatively from the material (Formula IV).

Process 4

The compound (Formula V) obtained by the process 3 and 3,5-di-tert-butyl-4-methoxymethyloxybenzoyl chloride are caused to react preferably in the presence of a base and at temperatures of 0°–100° C. in a solvent which dissolves both compounds or solventless condition to give a compound (Formula VI). As a base, preferably nitrogen compound without having active hydrogen, more suitably such as triethylamine or pyridine, can be used.

Process 5

The compound (Formula VI) obtained by the process 4 is treated in the presence of a base and at temperatures of 0°–100° C. in a solvent which dissolves the base to give the aimed intermediate (Formula VII). As a base, alkali metal hydroxide, such as potassium hydroxide or sodium hydroxide, can be preferably used.

Then, processes 6–8 (Scheme II) to give aimed purine derivatives from the intermediate 2-(3,5-di-tert-butyl-4-methoxymethyloxyphenyl)-9-benzyl-6-hydroxypurine (Formula VII) which was obtained by the above-mentioned processes 1–5 are outlined below.

Scheme II

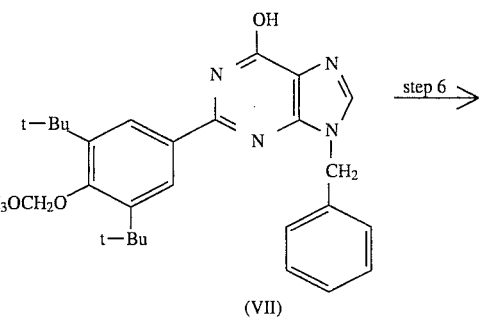

(VII)

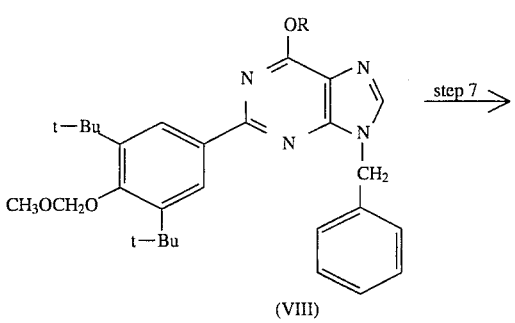

(VIII)

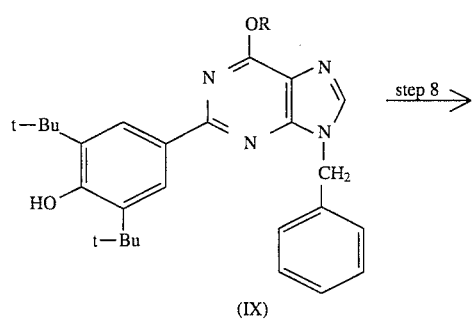

(IX)

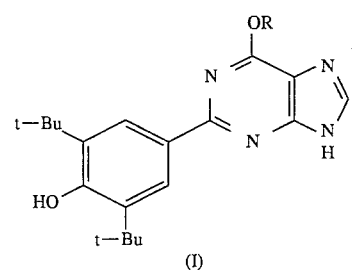

(I)

Process 6

The intermediate (Formula VII) obtained by processes 1–5 is reacted with compounds mentioned below selected according to the substituent R in the purine derivatives shown by general formula [I]. That is, when R represents an alkyl group in the aimed purine derivatives shown by general formula [I], the intermediate (VII) is reacted with a corresponding said alkyl p-toluenesulfonate, when R represents a carboxy group substituted alkyl group having one carboxy group in the aimed purine derivatives shown by general formula [I], the intermediate (VII) is reacted with a corresponding said alkanoic acid ester substituted with one halogen atom (said carboxyl substituted alkyl monohalide), and when R represents 4-carboxybenzyl group in the aimed purine derivatives shown by general formula [I], the intermediate (VII) is reacted with a corresponding ester of 4-halomethylbenzoic acid, or when R represents phenethyl group in the aimed purine derivative shown by general formula [I], the intermediate (VII) is reacted with a corresponding said phenethyl p-toluenesulfonate. The reactions are carried out preferably in the presence of a base and at temperatures of 0°–100° C. in a solvent which dissolves both compounds or solventless condition to give compounds (Formula VIII). As a base, nitrogen compound without having active hydrogen such as triethylamine or pyridine, or an alkali metal carbonate such as potassium carbonate can be suitably used. In addition, compounds (Formula VIII) may preferably be purified by a column chromatography and used for the next process, if necessary.

In addition, when R represents a substituted alkyl group having one carboxyl group, a corresponding said alkanoic acid ester substituted with one halogen atom (said carboxyl substituted alkyl monohalide), and when R represents 4-carboxybenzyl group, a corresponding ester of 4-halomethylbenzoic acid is reacted, respectively. Thus, the carboxyl group in the product is obtained as an ester which may be hydrolyzed with a strong base of alkali metal hydroxide such as potassium hydroxide or sodium hydroxide to provide alkyl group substituted with one carboxyl group or 4-carboxybenzyl group.

Process 7

The compounds (Formula VIII) being introduced with a substituent R and obtained in the process 6 are treated with an acid to give compounds (Formula IX) free from methoxymethyl group. A hydroacid such as trifluoroacetic acid and hydrochloric acid is preferably used. The resultant compounds (Formula IX) are preferably used for the next process after purification, for example column chromatography, if necessary.

Process 8

Hydrogenation of compounds (Formula IX) obtained by process 7 provides purine derivatives removed of benzyl group shown by general formula [I]. The above-mentioned reductive reaction is preferably carried out with hydrogen ($H_2$) in the presence of a catalytic amount of palladium carbon (Pd—C) or with formic acid. The final products shown by general formula [I] are preferably purified, for example, by a column chromatography, if necessary.

The purine derivatives shown by the general formula [I] in which R represents hydrogen atom, 2-(3,5-di-tert-butyl-4-hydroxyphenyl)-6-hydroxypurine, can be obtained directly from above-mentioned intermediate (Formula VII) by performing processes 7 and 8 without process 6.

The purine derivatives and pharmacologically acceptable salts thereof of the present invention may take forms of solid, semi-solid or liquid pharmaceutical preparations by admixing to conventional organic or inorganic carriers or fillers suitable for oral, parenteral or external administration. Aforementioned conventional pharmaceutical preparations are used as oral, parenteral or external preparations. For example, tablets, pellets, capsules, patches, solution preparations, emulsions, suspensions and the other forms suitable for the other conventional routes of administration, for example, inhalation spray preparations and suppositories. The carriers and fillers used for the preparations are suitably selected from conventional known carriers and fillers according to the forms and methods for administration. For example, water, glucose, lactose, gum arabic and gelatin may be illustrated. Furthermore, any carriers or fillers without causing chemical reaction with said purine derivatives or pharmacologically acceptable salts thereof can be used without restriction.

The dosages and effective doses of the purine derivatives or pharmacologically acceptable salts thereof can be decided according to the age, body weight, symptoms and route of administration of each patient. Generally, daily doses of about 0.1–100 mg/kg of the effective ingredient are used for the treatment of patients. The aforementioned doses may be divided several portions in a day according to the forms and routes of administration.

The pharmaceutical preparations prepared by the methods shown above and containing the purine derivatives or pharmacologically acceptable salts thereof of the present invention are used for the treatment of inflammatory diseases caused by leukocytes in the lesion as effective agents for the inhibition of inflammatory responses. The inflammatory diseases to be treated practically include allergic diseases such as asthma and dermatitis, pulmonary diseases such as adult respiratory distress syndrome (ARDS) and autoimmune diseases such as nephritis and rheumatism. The compositions are also useful for the inhibition and prevention of symptoms such as endotoxin shock and endotoxemia which cause aforementioned ARDS.

The purine derivatives and pharmacologically acceptable salts thereof of the present invention exhibit extensive activity for scavenging active oxygen with excellent properties for the prevention of lipid peroxidation, inhibition of $TXA_2$ synthesis, prevention of neutrophil adhesion, PAF antagonistic activity, and against endotoxin induced death, and effects on Masugi nephritis, nephrotoxininduced nephritis. Thus, these compounds are effective for the inhibition of inflammatory responses due to tissue damages caused by mediators such as active oxygen and $TXA_2$ released from activated leukocytes (neutrophils). Furthermore, these compounds prevent the adhesion of leukocytes to the cells in the inflammatory lesions and inhibit the aggravation of inflammatory responses caused by activated leukocytes (neutrophils). That is, these compounds prevent the tissue damages caused by mediators such as active oxygen and $TXA_2$ in the primary stage of inflammation and prevent the aggravation of inflammatory responses accompanied with the adhesion of activated leukocytes to the cells in the lesion exhibiting efficacy as drugs for the inhibition of inflammation in any stage of inflammatory diseases due to leukocytes.

EXAMPLES

Hereinafter, particularly effective purine derivatives of the invention for the inhibition of inflammatory responses and methods of their synthesis are explained by the examples. Furthermore, Test experiments for the evaluation of inhibitory effect of the purine derivatives of the present invention against inflammatory responses will be explained. However, the scope of the present invention is not restricted by these examples.

Example 1

Synthesis of
2-(3,5-di-tert-butyl-4-hydroxyphenyl)-6-methoxypurine

An intermediate 2-(3,5-di-tert-butyl-4-methoxymethyloxyphenyl)-9-benzyl-6-hydroxypurine (Formula VII ) was prepared by the following processes 1.1–1.5.

[Process 1.1]

In 200 ml of ethanol, 16.3 g (0.1 mol ) of 4-amino-5-imidazolecarboxamide monohydrochloride shown by formula [II] was suspended and dissolved by the addition of 27.8 ml (0.2 mol) of triethylamine. To the resultant solution, 10.2 ml (0.1 mol) of benzaldehyde was added and refluxed at 120° C. for 8 hrs. The reaction mixture was cooled to 0° C., added with 400 ml of water and stirred at 0° C. for 1 hr. The precipitate of product was collected by filtration, washed successively with water and ethanol, and dried to give 20.8 g of compound (Formula III) with a yield of 97% from 4-amino-5-imidazolecarboxamide.

[Process 1.2]

In a mixed solvent of 240 ml of DMF and 30 ml of water, 12.8 g (60 mmol) of the compound (Formula III) obtained by process 1.1 was suspended and 16.6 g (120 mmol) of potassium carbonate was added and then 13.8 ml of benzyl chloride was added dropwise with heating at 80° C. and stirred for 45 min. Then, the resulting reaction mixture was stirred at 80° C. for another 1 hr. The solvent in the reaction mixture was evaporated under reduced pressure to give a residue containing the product. The product in residue was extracted with chloroform and the extract was washed with water until the washings become neutral. The washed extract was evaporated under reduced pressure to distill off chloroform and recrystallized from ethanol to give 14.4 g of compound (Formula IV), with a yield of 79% from the compound (Formula III).

[Process 1.3]

In 150 ml of THF solution containing 1.2N-hydrochloric acid, 9.12 g (30 mmol) of the compound (Formula IV) obtained by the process 1.2 was added and the mixture was stirred at room temperature for 2 hrs. The precipitate of product was collected by filtration and washed with THF to give 7.26 g of the hydrochloride of compound (Formula V). The precipitate was dissolved in a mixture of 100 ml of methanol and 80 ml of water, and 7.5 ml of 4N-NaOH aqueous solution was added to the solution. The reaction mixture was stirred at room temperature for 1 hr. Then methanol in the reaction mixture was evaporated under reduced pressure to precipitate a compound shown by (Formula V). The precipitated compound (Formula V) was collected by filtration and washed successively with water and ethanol, and dried to give 5.85 g of compound (Formula V) with a yield of 90% from the compound (Formula IV).

[Process 1.4]

To 300 ml of pyridine, 15.2 g (70 mmol) of the compound (Formula V) obtained by the process 1.3 was added and suspended, and 50 ml of benzene solution of 3,5-di-tert-butyl-4-methoxymethyloxybenzoyl chloride (84 mmol) prepared from 3,5-di-tert-butyl-4-methoxymethyloxybenzoic acid was added. The resulting reaction mixture was stirred at room temperature for 6 hrs. Then, pyridine in the reaction mixture was evaporated under reduced pressure to give a residue containing the product. The product in the residue was extracted with chloroform and the extract was washed with water. The extract was evaporated to distill off chloroform and dried up under reduced pressure. The residue was recrystallized from ethanol to give 28.5 g of crystals of the compound (Formula VI) with a yield of 83% from the compound (Formula V).

$^1$H-NMR (DMSO-d$_6$, δppm): 1.43 (18H,s), 3.57 (3H,s), 4.89 (2H,s), 5.52 (2H,s), 7.17–7.35 (7H,m), 7.90 (2H,s), 7.95 (1H,s) and 10.25 (1H,s) which correspond to the signals presumed from the structure of the compound (Formula VI).

[Process 1.5]

In 750 ml of 0.1N KOH ethanolic solution, 14.8 g (30 mmol) of the compound (Formula VI) obtained by the process 1.4 was added and suspended, and the suspension was refluxed at 80° C. for 16 hrs. The reaction mixture was cooled to 0° C. and acidified by addition of 5 ml of acetic acid to precipitate crystals of compound (Formula VII). The crystals were collected by filtration, washed with ethanol to give 13.2 g of the compound (Formula VII) with a yield of 93% from the compound (Formula VI).

$^1$H-NMR (DMSO-d$_6$, δppm): 1.46 (18H,s), 3.58 (3H,s), 4.91 (2H,s), 5.60 (2H,s), 7.29–7.39 (5H,m), 8.00 (2H,s), 8.42 (1H,s) and 12.60 (1H,s) which correspond to the signals presumed from the structure of the compound (Formula VII).

A purine derivative, 2-(3,5-di-tert-butyl-4-hydroxyphenyl)-6-methoxypurine shown by general formula [I] in which R represents methyl group was prepared from an intermediate (Formula VII) in similar manners to those of processes 1.6 to 1.8.

[Process 1.6]

To 40 ml of DMF, 2.37 g (5.0 mmol) of the compound (VII) was added, and suspended, and 1.38 g (10 mmol) of potassium carbonate was added and stirred for 10 min. To the reaction mixture, 1.86 g (10 mmol) of methyl p-toluenesulfonate was added and stirred for 24 hrs at room temperature. Then, DMF was evaporated under reduced pressure to give a residue containing the product. The product was extracted from the residue with chloroform and the extract was washed with water. The washed extract was evaporated under reduced pressure to give a residue containing the product. The residue was purified by a silica gel column chromatography using an eluent mixture of chloroform and methanol at a volume ratio of 100:1 to give 951 mg of compound (Formula VIII, R=methyl group), 9-benzyl-2-(3,5-di-tert-butyl-4-methoxy-methyloxyphenyl)-6-methoxypurine with a yield of 39Z from the compound (Formula VII).

[Process 1.7]

To 950 mg (1.94 mmol) of a compound (Formula VIII, R=methyl group) obtained by process 1.6, 40 ml of 20 v/v % trifluoroacetic acid—dichloromethane mixture was added and stirred for 2 hrs at room temperature. Then, the reaction mixture was evaporated under reduced pressure to give a residue containing the product. The product in the residue was extracted with chloroform and the extract was successively washed with saturated sodium hydrogencarbonate aqueous solution and water. The washed extract was evaporated under reduced pressure to give a residue containing the product. The residue was purified by a silica-gel column chromatography using an eluent mixture of chloroform and methanol (100:1) to give 792 mg of a compound (Formula IX, R=methyl group), 9-benzyl-2-(3,5-di-tert-butyl-4-hydroxyphenyl)-6-methoxypurine with a yield of 92% from the compound (Formula VIII, R=methyl group).

[Process 1.8]

In 10 ml of DMF, 667 mg (1.5 mmol) of the compound (Formula IX, R=methyl group) was dissolved and 450 mg of 10 w/w% Pd—C was added. To the mixture, 2 ml of formic acid was added with stirring and further stirred for 2 hrs at room temperature. Then, 1 g of Super-Cel (diatomaceous earth) was added and the mixture was stirred for 10 min. The reaction mixture was filtered to give a filtrate. The filtrate was evaporated under reduced pressure to give a residue containing the product. The product was extracted from the residue with chloroform and the extract was successively washed with saturated sodium hydrogencarbonate aqueous solution and water. The washed extract was evaporated under reduced pressure to give a residue containing the product. The residue was purified by a silica-gel column chromatography using an eluent mixture of chloroform and methanol (50:1) and recrystallized from a mixture of ethanol—water to give 508 mg of a compound (Formula I, R=methyl group), 2-(3,5-di-tert-butyl-4-hydroxyphenyl)-6-methoxypurine with a yield of 96% from the compound (Formula IX, R=methyl group).

Melting point: 158°–161° C.

$^1$H-NMR (DMSO-d$_6$, δppm): 1.47 (18H,s), 4.18 (3H,s), 8.27 (1H,s), 8.30 (2H,s) and 13.34 (1H,s).

$^{13}$C-NMR (DMSO-d$_6$, δppm): 30.68, 35.37, 53.79, 125.71, 129.57, 138.39, 142.57, 157.08 and 160.04.

These signals correspond to those presumed from the structure of the compound (Formula I) in which R represents methyl group.

Elemental analysis for C$_{20}$H$_{26}$N$_4$O$_2$·H$_2$O

|  | C(%) | H(%) | N(%) |
| --- | --- | --- | --- |
| Calculated | 64.49 | 7.58 | 15.04 |
| Found | 64.61 | 7.72 | 14.96 |

Example 2

Preparation of 2-(3,5-di-tert-butyl-4-hydroxyphenyl)-6-n-propoxypurine

[Process 2.1]

In DMF solvent, an intermediate compound (Formula VII), 2-(3,5-di-tert-butyl-4-methoxymethyloxyphenyl)-9-benzyl-6-hydroxypurine (Formula VII), and n-propyl p-toluenesulfonate were reacted in a similar manner to that of process 1.6 in the Example 1 in the presence of a base; potassium carbonate and the product was purified to give compound shown by formula (VIII, R : n-propyl), 9-benzyl-2-(3,5-di-tert-butyl-4-methoxymethyloxypenyl)-6-n-propoxypurine.

[Process 2.2]

The compound (Formula VIII, R=n-propyl) prepared by process 2.1 was treated with trifluoroacetic acid in a similar manner to that of process 1.7 in the above-mentioned Example 1 and obtained a compound (Formula IX, R=n-propyl group) by this deblocking of methoxymethyl group. The compound (IX, R=n-propyl) was hydrogenated in a similar manner to that of process 1.8 in the above-mentioned Example 1 and obtained crystals of a debenzylated compound (Formula I, R=n-propyl group), 2-(3,5-di-tert-butyl-4-hydroxyphenyl)-6-n-propoxypurine. The total yield of final compound from the compound (Formula VII) was estimated as 73% from the respective yield of above-mentioned processes 2.1 and 2.2.

Melting point: 141°–143° C.

$^1$H-NMR (DMSO-d$_6$, δppm): 1.04 (3H,t), 1.46 (18H,s), 1.91 (2H,m), 4.61 (2H, t), 7.34 (1H,s), 8.26 (1H,s), 8.28 (2H,s) and 13.34 (1H,s).

$^{13}$C-NMR (CDCl$_3$, δppm): 10.58, 22.37, 30.44, 34.67, 68.93, 125.61, 128.27, 136.33, 140.04, 153.16, 156.66, 159.73 and 160.58.

These signals correspond to those of presumed from the structure of the compound (Formula I) in which R represents n-propyl group.

Elemental analysis for C$_{22}$H$_{30}$N$_4$O$_2$·1/4H$_2$O

|  | C(%) | H(%) | N(%) |
| --- | --- | --- | --- |
| Calculated | 68.28 | 7.94 | 14.48 |
| Found | 68.43 | 8.06 | 14.38 |

Example 3

Preparation of 6-n-butoxy-2-(3,5-di-tert-butyl-4-hydroxyphenyl)purine

[Process 3.1]

In DMF solvent, the intermediate compound (Formula VII) and n-butyl p-toluenesulfonate were reacted in a similar manner to that of process 1.6 in the above-mentioned Example 1 in the presence of a base; potassium carbonate and the product was purified to give a compound shown by formula (VIII, R=n-butyl), 9-benzyl-6-n-butoxy-2-(3,5-di-tert-butyl-4-methoxymethyloxyphenyl)purine.

[Process 3.2]

The compound (Formula VIII, R=n-butyl) prepared by process 3.1 was treated with trifluoroacetic acid in a similar manner to that of process 1.7 in the above-mentioned Example 1 and obtained a compound (Formula IX, R=n-butyl group) by the deblocking of methoxymethyl group. The compound (IX, R=n-buryl) was hydrogenated by a similar manner to that of process 1.8 in the above-mentioned Example 1 and obtained crystals of a compound (Formula I, R=n-butyl group), 6-n-butoxy-2-(3,5-di-tert-butyl-4-hydroxyphenyl)purine. The total yield of final compound from the compound (Formula VII) was estimated as 73% from the respective yield of above-mentioned processes 3.1 and 3.2.

Melting point: 129°–134° C.

$^1$H-NMR (DMSO-d$_6$, δppm): 0.98 (3H, t), 1.46 (18H,s), 1.50 (2H,m), 1.86 (2H,m), 4.66 (2H,t), 7.34 (1H,s), 8.25 (1H,s), 8.28 (2H,s) and 13.31 (1H,s).

$^{13}$C-NMR (DMSO-d$_6$, δppm): 13.66, 18.77, 30.28, 30.57, 34.58, 65.56, 124.37, 128.78, 138.33, 155.89 and 157.85.

These signals correspond to those presumed from the structure of the compound (Formula I) in which R represents n-butyl group.

Elemental analysis for C$_{23}$H$_{32}$N$_4$O$_2$

|  | C(%) | H(%) | N(%) |
| --- | --- | --- | --- |
| Calculated | 69.67 | 8.13 | 14.13 |
| Found | 69.65 | 8.24 | 14.12 |

Example 4

Preparation of 2-(3,5-di-tert-butyl-4-hydroxyphenyl)-6-n-hexyloxypurine

[Process 4.1]

In DMF solvent, the intermediate compound (Formula VII) and n-hexyl p-toluenesulfonate were reacted in a similar manner to that of process 1.6 in the above-mentioned Example 1 in the presence of a base; potassium carbonate and the product was purified to give a compound shown by formula (VIII, R=n-hexyl), 9-benzyl-2-(3,5-di-tert-butyl-4-methoxymethyloxyphenyl)-6-n-hexyloxypurine.

[Process 4.2]

The compound (Formula VIII, R=n-hexyl) prepared by process 4.1 was treated with trifluoroacetic acid in a similar manner to that of process 1.7 in the above-mentioned Example 1 and obtained a compound (Formula IX, R=n-hexyl group). The compound (IX, R=n-hexyl) was hydrogenated by a similar manner to that of process 1.8 in the above-mentioned Example 1 and obtained crystals of a compound (Formula I, R=n-hexyl group), 2-(3,5-di-tert-butyl-4-hydroxyphenyl)-6-n-hexyloxypurine by debenzylation. The total yield of final compound from the compound (Formula VII) was estimated as 40% from the respective yield of above-mentioned processes 4.1 and 4.2.

Melting point: 185°–185.5° C.

$^1$H-NMR (DMSO-d$_6$, δppm): 0.87 (3H,t), 1.30–1.60 (6H, m), 1.46 (18H,s), 1.88 (2H,m), 4.65 (2H,t), 7.34 (1H,s), 8.25 (1H,s), 8.28 (2H,s) and 13.31 (1H,s).

13C-NMR (DMSO-d$_6$, δppm): 13.86, 22.13, 25.14, 28.48, 30.24, 31.02, 34.54, 55.78, 124.32, 128.71,138.31, 155.89 and 157.85.

These signals correspond to those presumed from the structure of the compound (Formula I) in which R represents n-hexyl group.

Elemental analysis for $C_{25}H_{36}N_4O_2$

|  | C(%) | H(%) | N(%) |
|---|---|---|---|
| Calculated | 70.72 | 8.55 | 13.20 |
| Found | 70.64 | 8.58 | 13.15 |

Example 5

Preparation of 2-(3,5-di-tert-butyl-4-hydroxyphenyl)-6-n-octyloxy-purine

[Process 5.1]

In DMF solvent, the intermediate raw material compound (Formula VII) and n-octyl p-toluenesulfonate were reacted in a similar manner to that of process 1.6 in the above-mentioned Example 1 in the presence of a base; potassium carbonate and the product was purified to give a compound shown by formula (VIII, R=n-octyl), 9-benzyl-2-(3,5-di-tert-butyl-4-methoxymethyloxyphenyl)-6-n-octyloxypurine.

[Process 5.2]

The compound (Formula VIII, R=n-octyl) prepared by process 5.1 was treated with trifluoroacetic acid in a similar manner to that of process 1.7 in the above-mentioned Example 1 and obtained a compound (Formula IX, R=n-octyl group). The compound (IX, R=n-octyl) was hydrogenated by a similar manner to that of process 1.8 in the above-mentioned Example 1 and obtained crystals of a compound (Formula I, R=n-octyl group), 2-(3,5-di-tert-butyl-4-hydroxy-phenyl)-1-n-octyloxypurine. The total yield of final compound from the compound (Formula VII) was estimated as 38% from the respective yield of above-mentioned processes 5.1 and 5.2.

Melting point: 155.5° C.

$^1$H-NMR (DMSO-d$_6$, δppm): 0.84 (3H, t), 1.20–1.60 (10H,m), 1.46 (18H,s), 1.87 (2H,m), 4.65 (2H,t), 7.35 (1H, s), 8.25 (1H,s), 8.28 (2H,s) and 13.31 (1H,s).

$^{13}$C-NMR (DMSO-d$_6$, δppm): 13.88, 22.05, 25.47, 28.54, 28.72, 30.24, 31.20, 34.54, 65.73, 124.32, 128.74, 138.28, 155.89 and 157.87.

These signals correspond to those presumed from the structure of the compound (Formula I) in which R represents n-octyl group.

Elemental analysis for $C_{27}H_{40}N_4O_2$

|  | C(%) | H(%) | N(%) |
|---|---|---|---|
| Calculated | 71.64 | 8.91 | 12.38 |
| Found | 71.63 | 9.00 | 12.33 |

Example 6

Preparation of 2-(3,5-di-tert-butyl-4-hydroxyphenyl)-6-phenethyl-oxypurine

[Process 6.1]

In DMF solvent, the intermediate compound (Formula VII) and phenethyl p-toluenesulfonate were reacted in a similar manner to that of process 1.6 in the above-mentioned Example 1 in the presence of a base; potassium carbonate and the product was purified to give a compound shown by formula (VIII, R=phenethyl), 9-benzyl-2-(3,5-di-tert-butyl-4-methoxymethyloxyphenyl)-6-phenethyloxypurine.

[Process 6.2]

The compound (Formula VIII, R=phenethyl) prepared by process 6.1 was treated with trifluoroacetic acid in a similar manner to that of process 1.7 in the above-mentioned Example 1 and obtained a compound (Formula IX, R=n-hexyl group) by the deblocking of methoxymethyl group. The compound (IX, R=phenethyl) was hydrogenated by a similar manner to that of process 1.8 in the above-mentioned Example 1 and obtained crystals of a debenzylated compound (Formula I, R=phenethyl group), 2-(3,5-di-tert-butyl-4-hydroxyphenyl)-6-phenethyloxypurine. The total yield of final compound from the compound (Formula VII) was estimated as 39% from the respective yield of above-mentioned processes 6.1 and 6.2.

Melting point: 155.5° C.

$^1$H-NMR (DMSO-d$_6$, δppm): 1.46 (18H,s), 3.20 (2H,m), 4.88 (2H,t), 7.36 (1H,s), 7.24–7.38 (5H,m), 8.25 (1H,s), 8.28 (2H,s) and 13.33 (1H,s).

$^{13}$C-NMR (DMSO-d$_6$, δppm): 30.30, 34.58, 34.71, 66.24, 124.43, 125.30, 128.27, 128.80, 137.85, 138.39, 155.98 and 158.00.

These signal correspond to those presumed from the structure of the compound (Formula I) in which R represents phenethyl group.

Elemental analysis for $C_{27}H_{32}N_4O_2 \cdot 1/4H_2O$

|  | C(%) | H(%) | N(%) |
|---|---|---|---|
| Calculated | 72.21 | 7.30 | 12.48 |
| Found | 72.22 | 7.33 | 12.51 |

Example 7

Preparation of 2-(3,5-di-ter-butyl-4-hydroxyphenyl)-6-hydroxypurine

[Process 7]

In 50 ml of DMF, 4.28 g (8 mmol) of an intermediate (Formula IX, R=phenethyl group), 9-benzyl-2-(3,5-di-tert-butyl-4-methoxymethyloxy)-6-phenethyloxypurine, obtained above-mentioned Process 6.2 in Example 6 was dissolved and 1 g of 10 w/w % Pd—C was added. To the mixture, 5 ml of formic acid was added with stirring and further stirred for 6 hrs at 60° C. Then, 2 g of Super-Cel was added and the mixture was stirred for 10 min. The reaction mixture was filtered to give a filtrate. The filtrate was evaporated under reduced pressure to give a residue containing the product. The product in the residue was extracted with chloroform and the extract was successively washed with saturated sodium hydrogencarbonate aqueous solution and water. The washed extract was evaporated under reduced pressure to give a residue containing the product. The residue was purified by a silica-gel column chromatography using an eluent mixture of chloroform and methanol (50:1) and recrystallized from a mixture of ethanol-water to give 2.44 g of a compound (Formula I) in which R represents H atom, 2-(3,5-di-tert-butyl-4-hydroxyphenyl)-6-hydroxypurine (Formula I, R=H atom), with a yield of 71z from the compound (Formula IX, R =phenethyl group).

Melting point: over 300° C.

$^1$H-NMR (DMSO-$d_6$, δppm): 1.44 (18H,s), 7.48 & 7.54 (1H,s), 7.82 (2H,s), 7.99 & 8.21 (1H,s), 12.36 & 12.43 (1H,s) and 13.16 & 13.38 (1H,s).

$^{13}$C-NMR (DMSO-$d_6$, δppm): 30.21, 34.76, 124.65, 138.61 and 156.60.

These signals correspond to those presumed from the structure of the compound (Formula I) in which R represents H atom. In addition, said compound showed two isomer forms of 9-NH and 7-NH in its solution and overlapped spectra of two forms were observed in $^1$H-NMR.

Elemental analysis for $C_{19}H_{24}N_4O_2 \cdot 2/3H_2O$

|  | C(%) | H(%) | N(%) |
| --- | --- | --- | --- |
| Calculated | 64.75 | 7.25 | 15.0 |
| Found | 64.89 | 7.24 | 15.83 |

Example 8

Preparation of 6-(3-carboxy-n-propoxy)-2-(3,5-di-tert-butyl-4-hydroxyphenyl)purine A purine derivative of general formula [I] in which R represents 3-carboxy-n-propyl group, 6-(3-carboxy-n-propoxy)-2-(3,5-di-tert-butyl-4-hydroxyphenyl)purine was prepared by the following processes 8.1–8.3 from the starting intermediate (Formula VII).

[Process 8.1]

In 72 ml of DMF, 5.70 g (12 mmol) of the intermediate (Formula VII) was suspended, 3.30 g (24 mmol) of potassium carbonate was added and the resultant mixture was stirred for 10 min. To the reaction mixture, 4.68 g (24 mmol) of ethyl 4-bromo-n-butyrate was added and stirred at room temperature for 20 hrs. Then, the reaction mixture was evaporated under reduced pressure to provide a residue containing the product. The product was extracted from the residue with chloroform and the extract was washed with water. The washed extract was evaporated under reduced pressure to give a residue containing the product. The residue was dissolved in a mixture of 25 ml of methanol and 20 ml of dioxane, and 5 ml of 10N-NaOH aqueous solution was added with stirring. The resulting reaction mixture was further stirred at room temperature for 6 hrs, then acidified by the addition of 8 ml of 6N-HCl. To the reaction mixture, 50 ml of water was added to give precipitate of the product. The precipitate was collected by filtration and dried to give a product shown by formula (VIII, R=3-carboxy-n-propyl group), 9-benzyl-6-(3-carboxy-n-propoxy)-2-(3,5-di-tert-butyl-4-methoxymethyloxyphenyl)purine.

[Process 8.2]

To the compound (Formula VIII, R=3-carboxy-n-propyl group) obtained in process 8.1, 100 ml of 20 v/v % trifluoroacetic acid—dichloromethane mixture was added and the mixture was stirred at room temperature for 2 hrs. Then, the reaction mixture was evaporated under reduced pressure to give a residue containing the product. The product in the residue was extracted with chloroform and the extract was successively washed with saturated sodium hydrogencarbonate aqueous solution and water. The washed extract was evaporated under reduced pressure to give a residue containing the product. The residue was dispersed in ethanol, and undissolved solid mass of the product was collected by filtration and dried to give 3.92 g of the resultant compound (Formula IX, R=3-carboxy-n-propyl group), 9-benzyl -6- (3-carboxy-n-propoxy) -2- ( 3,5-di-tert-butyl-4-hydroxyphenyl)purine, with a yield of 63% from the intermediate (VII).

[Process 8.3]

In 35 ml of DMF, 3.87 g (7.5 mmol) of the compound (Formula IX, R=3-carboxy-n-propyl group) obtained by above mentioned process 8.2 was dissolved and 1.0 g of 10 w/w % Pd—C was added. To the mixture, 3.5 ml of formic acid was added with stirring and further stirred at room temperature for 24 hrs. Then, 2 g of Super-Cel was added and the mixture was stirred for 10 min. The reaction mixture was filtered to give a filtrate. The filtrate was evaporated under reduced pressure to give a residue containing the product. The product in the residue was extracted with chloroform and the extract was successively washed with saturated sodium hydrogencarbonate aqueous solution and water. The washed extract was evaporated under reduced pressure to remove chloroform and to give a residue containing the product. The residue was dispersed and suspended in ethanol and the product was collected by filtration and recrystallized from a mixture of ethanol-water to give 2.69 g of crystals of a compound (Formula I, R =3-carboxy-n-propyl group), 6-(3-carboxy-n-propoxy)-2-(3,5-di-tert-butyl-4-hydroxyphenyl)purine with a yield of 84% from the compound (Formula IX, R=3-carboxy-n-propyl group).

Melting point: 247°–247.5° C.

$^1$H-NMR (DMSO-$d_6$, δppm): 1.46 (18H,s), 2.12 (2H,m), 2.45 (2H,t), 4.66 (1H,s), 8.27 (3H,s), 12.18 (1H,s) and 13.33 (1H,s).

$^{13}$C-NMR (DMSO-$d_6$, δppm): 24.13, 30.30, 34.60, 65.18, 124.37, 128.65, 138.37, 155.96, 157.89 and 173.83.

These signals correspond to those presumed from the structure of the compound (Formula I) in which R represents 3-carboxy-n-propyl group.

Elemental analysis for $C_{23}H_{30}N_4O_4$

|  | C(%) | H(%) | N(%) |
| --- | --- | --- | --- |
| Calculated | 64.77 | 7.09 | 13.14 |
| Found | 64.78 | 7.13 | 13.18 |

Example 9

Preparation of 6-(5-carboxy-n-pentyloxy)-2-(3,5-di-tert-butyl-4-hydroxyphenyl)purine

[Process 9.1]

The intermediate compound (Formula VII) and ethyl 6-bromo-n-hexanoate were reacted in a similar manner to that of process 8.1 in the above-mentioned Example 8 in the presence of a base; potassium carbonate and the product was hydrolyzed with sodium hydroxide to give a compound shown by formula (VIII, R=5-carboxy-n-pentyl group), 9-benzyl-6-(5-carboxy-n-pentyloxy)-2-(3,5-di-tert-butyl-4-methoxymethyloxyphenyl)purine.

[Process 9.2]

The compound (Formula VIII, R=5-carboxy-n-pentyl group) prepared by process 9.1 was treated with trifluoroacetic acid in a similar manner to that of process 8.2 in the above Example 8 and obtained a compound (Formula IX, R=5-carboxy-n-pentyl group) by the deblocking of methoxymethyl group. The compound (IX, R=5-carboxy-n-pentyl group) was hydrogenated by a similar manner to that of process 8.3 in the above Example 8 and obtained crystals of a debenzylated compound (Formula I, R=5-carboxy-n-pentyl group), 6-(5-carboxy-n-pentyloxy)-2-(3,5-di-tert-butyl-4-hydroxyphenyl)purine. The total yield of final compound from the intermediate (Formula VII) was estimated as 62% from the respective yield of above-mentioned processes 9.1 and 9.2.

Melting point: 231°–232° C.

$^1$H-NMR (DMSO-d$_6$, δppm): 1.46 (18H,s), 1.40–1.70 (4H,m), 1.89 (2H,m), 2.25 (2H,t), 4.65 (2H,t), 7.34 (1H,s), 8.26 (1H,s), 8.28 (2H,s), 12.01 (1H,s) and 13.31 (1H,s).

$^{13}$C-NMR (DMSO-d$_6$, δppm): 24.46, 25.30, 28.44, 30.37, 33.77, 34.65, 65.87, 124.50, 128.85, 138.40, 156.04, 158.08 and 174.33.

These signals correspond to those presumed from the structure of the compound (Formula I) in which R represents 5-carboxy-n-pentyl group.

Elemental analysis for $C_{25}H_{34}N_4O_4$

|  | C(%) | H(%) | N(%) |
| --- | --- | --- | --- |
| Calculated | 66.05 | 7.54 | 12.33 |
| Found | 66.16 | 7.58 | 12.25 |

Example 10

Preparation of 6-(7-carboxy-n-heptyloxy)-2-(3,5-di-tert-butyl-4-hydroxyphenyl)purine

[Process 10.1]

The intermediate compound (Formula VII) and ethyl 8-bromo-n-octanoate were reacted in DMF in a similar manner to that of process 8.1 in the above-mentioned Example 8 in the presence of a base; potassium carbonate and the produced ester was hydrolyzed using sodium hydroxide to give a compound shown by formula (VIII, R=7-carboxy-n-heptyl group), 9-benzyl-6-(7-carboxy-n-heptyloxy)-2-(3,5-di-tert-butyl-4-methoxymethyloxyphenyl)purine.

[Process 10.2]

The compound (Formula VIII, R 7-carboxy-n-heptyl group) prepared by process 10.1 was treated with trifluoroacetic acid in a similar manner to that of process 8.2 in the above Example 8 and obtained a compound (Formula IX, R=7-carboxy-n-heptyl group) by the deblocking of methoxymethyl group. The compound (IX, R=7-carboxy-n-heptyl group) was hydrogenated by a similar manner to that of process 8.3 in the above Example 8 and obtained crystals of a debenzylated compound (Formula I, R=7-carboxy-n-heptyl group), 6-(7-carboxy-n-heptyloxy)-2-(3,5-di-tert-butyl-4-hydroxyphenyl)purine. The total yield of final compound from the intermediate (Formula VII) was estimated as 59% from the respective yield of above-mentioned processes 10.1 and 10.2.

Melting point: 216°–217° C.

$^1$H-NMR (DMSO-d$_6$, δppm): 1.46 (18H,s), 1.20–1.60 (8H,m), 1.88 (2H,m), 2.19 (2H,t), 4.65 (2H,t), 7.33 (1H,s), 8.25 (1H,s), 8.28 (2H,s), 11.97 (1H,s) and 13.31 (1H,s).

$^{13}$C-NMR (DMSO-d$_6$, δppm): 24.53, 25.49, 28.59, 28.68, 30.34, 33.70, 34.61, 65.91, 124.45, 128.84, 138.37, 155.98, 158.02 and 174.37.

These signals correspond to those presumed from the structure of the compound (Formula I) in which R represents 7-carboxy-n-heptyl group.

Elemental analysis for $C_{27}H_{38}N_4O_4 \cdot 1/5H_2O$

|  | C(%) | H(%) | N(%) |
| --- | --- | --- | --- |
| Calculated | 66.69 | 7.96 | 11.53 |
| Found | 66.85 | 7.94 | 11.40 |

Example 11

Preparation of 6-(4-carboxybenzyloxy)-2-(3,5-di-tert-butyl-4-hydroxyphenyl)purine The purine derivative of general formula [I] in which R represents 4-carboxybenzyl group, 6-(4-carboxy-benzyloxy)-2-(3,5-di-tert-butyl-4-hydroxyphenyl)purine was prepared by the following processes 11.1–11.3 from the starting intermediate (Formula VII).

[Process 11.1]

In 18 ml of DMF, 1.42 g (3 mmol) of the intermediate compound (Formula VII) was suspended, 829 mg (6 mmol) of potassium carbonate was added and stirred for 10 min. To the suspension, 1.37 g (6 mmol) of methyl 4-bromomethylbenzoate was added and the mixture was stirred at room temperature for 20 hrs. The reaction mixture was evaporated under reduced pressure to remove DMF and a residue containing the product was obtained. The product was extracted from the residue with chloroform and the extract was washed with water. The washed extract was evaporated to dryness under reduced pressure to give a residue containing the product. The residue was dissolved in a mixture of 15 ml of methanol and 12 ml of dioxane, and 3 ml of 10N sodium hydroxide aqueous solution was added with stirring and further stirred at room temperature for 6 hrs. The resulting solution was acidified by addition of 5 ml of 6N hydrochloric acid. The solution was evaporated under reduced pressure to give a residue. The product in the residue was extracted with chloroform and the extract was washed with water. Further, the washed extract was evaporated under reduced pressure to give a residue. The product recovered as a residue was a compound of general formula [VIII, R=4-carboxybenzyl group], 9-benzyl-6-(4-carboxybenzyloxy)-2-(3,5-di-tert-butyl-4-methoxymethyloxyphenyl)purine.

[Process 11.2]

A mixture of the product recovered as a residue in process 11.1 and 50 ml of 20 v/v % mixture of trifluoroacetic acid—dichloromethane was stirred at room temperature for 2 hrs. The reaction mixture was evaporated under reduced pressure to give a residue containing the product. The product in the residue was extracted with chloroform and the extract was washed successively with saturated sodium hydrogencarbonate aqueous solution and water. The washed extract was evaporated under reduced pressure to give a residue containing the product. The residue was poured into ethanol, and undissolved precipitate of the product was collected by filtration and dried to give 825 mg of the resultant compound (Formula IX, R=4-carboxybenzyl group), 9-benzyl-6-(4-carboxybenzyloxy)-2-(3,5-di-tert-butyl-4-hydroxyphenyl)purine, with a yield of 49% from the intermediate (VII).

[Process 11.3]

In 6 ml of DMF, 564 mg (1.0 mmol) of a compound (Formula IX, R=4-carboxybenzyl group) obtained by process 11.2 was dissolved and 300 mg of 10 w/w % Pd—C was added. To the mixture, 0.6 ml of formic acid was added with stirring and the mixture was further stirred at room temperature for 36 hrs. Then, 1 g of Super-Cel was added and the mixture was stirred for 10 min. The reaction mixture was filtered to give a filtrate. The filtrate was evaporated under reduced pressure to give a residue containing the product. The product in the residue was extracted with chloroform and the extract was successively washed with saturated sodium hydrogencarbonate aqueous solution and water. The washed extract was evaporated under reduced pressure to give a residue containing the product. The residue was purified by a silica-gel column chromatography using an eluent mixture of dichloromethane and methanol (50:1) and recrystallized to give 65 mg of compound of general formula [I, R=4-carboxybenzyl group], 6-(4-carboxybenzyl-oxy)-2-(3,5-di-tert-butyl-4-hydroxyphenyl)purine with a yield of 14% from the compound (Formula IX, R=4-carboxybenzyl group).

Melting point: 297°–298° C.

$^1$H-NMR (DMSO-$d_6$, δppm): 1.44 (18H,s), 5.82 (2H,s), 7.33 (1H,s), 7.66 (2H,d), 7.96 (2H,d), 8.22 (2H,s), 8.34 (1H,s), 12.96 (1H,s) and 13.40 (1H,s).

$^{13}$C-NMR (DMSO-$d_6$, δppm): 30.30, 34.58, 66.52, 124.41, 127.55, 128.50, 129.40, 130.16, 138.40, 141.93, 156.02, 157.87 and 166.89.

These signals correspond to those presumed from the structure of the compound (Formula I) in which R represents 4-carboxybenzyl group.

Elemental analysis for $C_{27}H_{30}N_4O_4 \cdot H_2O$

|  | C(%) | H(%) | N(%) |
|---|---|---|---|
| Calculated | 65.83 | 6.55 | 11.38 |
| Found | 65.97 | 6.23 | 11.33 |

The biological activities of the purine derivatives of the present invention were evaluated for preventive effect of lipid peroxidation, inhibition of $TXA_2$ synthesis, prevention of adhesion of neutrophils to endothelial cells, anti-PAF activity, inhibition against endotoxin induced death, and effect on nephrotoxin induced serum nephritis. The Test Examples for the compounds disclosed in the above Examples will be described below.

Test Example 1

(Scavenging of active oxygen)

Inhibitory effect against lipid peroxidation was evaluated by the method shown below to examine the activity of scavenging active oxygen of purine derivatives of the present invention.

The inhibitory effect against oxidation of linolenic acid to conjugated diene due to hydroxy radical (.OH) formed by Fenton reaction was determined according to the method of Kharasch et al. (see J. Biol. Chem., 2.60, 10,645 (1985)). A predetermined concentration of $FeCl_2$ solution was added to a mixture of water and DMSO containing predetermined amount of linolenic acid, NaCl, $H_2O_2$, Lubrol and the rest compound to start the reaction. Above-mentioned compounds were dissolved to give initial concentrations of 1.0 mM for linolenic acid, 30 mM for NaCl, 100 μM for $H_2O_2$, 80 μM for $FeCl_2$, 0.08% for Lubrol, and 1 v/v % for DMSO, respectively. Then, the changes of absorbance at 234 nm due to the formation of conjugated diene in the reaction solutions were determined periodically. The inhibitory rate (%) was estimated from the differences between the test solutions and corresponding solutions without the test compound. When the difference of said reaction rate was 0 (zero), then the inhibitory rate was made 0%, and when the reaction rate was 0 (zero), then the inhibitory rate was made 100%.

The inhibitory rate was estimated for various concentrations of said test compounds and the 50%-inhibitory concentration ($IC_{50}$) was regressively calculated. The preventive effect against lipid peroxidation was evaluated using $IC_{50}$. The $IC_{50}$s of compounds in Example 1–11 were listed in Table 1. The $IC_{50}$ of probucol was made as positive control and also shown in Table 1.

TABLE 1

| Test compound shown by Example No. | $IC_{50}$ (M) |
|---|---|
| Example 1 | $3.5 \times 10^{-6}$ |
| Example 2 | $3.4 \times 10^{-6}$ |
| Example 3 | $3.5 \times 10^{-6}$ |
| Example 4 | $3.7 \times 10^{-6}$ |
| Example 5 | $5.4 \times 10^{-6}$ |
| Example 6 | $3.5 \times 10^{-6}$ |
| Example 7 | $3.4 \times 10^{-6}$ |
| Example 8 | $4.0 \times 10^{-6}$ |
| Example 9 | $3.6 \times 10^{-6}$ |
| Example 10 | $3.7 \times 10^{-6}$ |
| Example 11 | $3.9 \times 10^{-6}$ |
| Probucol | $2.5 \times 10^{-6}$ |

In the above evaluation method, the test compounds and an active oxygen source of hydroxy radical mainly react to lower the hydroxy radical concentration in the reaction mixture indicating the inhibitory effect on the oxidation reaction of linolenic acid. In addition, the other active oxygen sources such as HOCl (hypochlorite), OO$^-$ (superoxide radical), $O_2^*$ ($^1O_2$ singlet oxygen) are presumed to react with said test compounds and inactivate them.

Reaction (a)

$Cl^- + .OH \rightarrow Cl. + OH^-$ $Cl. + Cl. \rightarrow Cl_2$ $Cl_2 +^{-OH \rightarrow Cl^-} + HOCl$ Reaction (b)

$Fe^{3+} + H_2O_2 \rightarrow Fe^{3+} - {}^-OOH + H^+$ $Fe^{3+} - {}^-OOH \rightarrow Fe^{2+} + OOH$ $OOH \rightarrow OO^- + H^+$ Reaction (c)

$2OO^- + H^+ \rightarrow {}^-OOH + O_2^*$

Reaction (d)

$HOCl + {}^-OOH \rightarrow H_2O + Cl^- + O_2^*$

As shown in Table 1, purine derivatives of the present invention shown in Examples 1–11 exhibited preventive effect against lipid peroxidation. In addition, these data exhibit their scavenging activity against active oxygen. Furthermore, the activity of scavenging active oxygen of compounds shown in Example 1–11 are comparably as superior as that of probucol.

Test Example 2

(Inhibition of $TXA_2$ synthesis)

Inhibitory effect against $TXA_2$ synthesis was evaluated by the method shown below determining the formation of $TXA_2$ as an arachidonic acid metabolite in the presence of purine derivatives of the present invention.

$TXA_2$ (thromboxane $A_2$) is reported to be synthesized by $TXA_2$ synthetase in arachidonic acid cascade via a cyclic peroxide ($PGH_2$) formed by cyclooxygenase system. Crude $TXA_2$ synthetase was prepared by the following method in the present invention. Blood drawn from healthy volunteer was centrifuged at 200 G for 15 min. and the resulting supernatant was further centrifuged at 2,000 G for 10 min. to give precipitates. The precipitates were homogenized in 0.01M phosphate buffer and centrifuged at 1,000 G for 10 min. to give a supernatant. The resultant supernatant was used as a crude $TXA_2$ synthetase in the following processes. The crude $TXA_2$ synthetase exhibiting a predetermined enzymic activity was mixed with predetermined amounts of labeled arachidonic acid and the test compound to give a reaction solution. The reaction solution was incubated at 37° C. for 10 min. and $TXA_2$ formed in the reaction mixture was determined by RIA method using a commercially available kit (Amersham Co., Ltd., RIA kit). The inhibitory rate was calculated from the difference between the determined amount of formed $TXA_2$ and that carried out in the absence of the test compound. When the difference of formed amount of $TXA_2$ was 0 (zero), then the inhibitory rate was made 0% and when the formation of $TXA_2$ was equal to that of solvent control without $TXA_2$ synthetase, then the inhibitory rate was made 100%.

The inhibitory rate was estimated for various concentrations of said test compounds and the concentration of 50%-inhibition ($IC_{50}$) was regressively calculated. The inhibitory effect against $TXA_2$ formation was evaluated using $IC_{50}$. The $IC_{50}$s of compounds obtained by Example 1–11 having particularly high inhibitory rate were listed in Table 2. The $IC_{50}$ of ozagrel hydrochloride, which is disclosed in J. Med. Chem., 24, 1139–1149 (1981) and exhibit very high inhibitory effect against $TXA_2$ synthesis, is also shown in Table 2 as a positive control.

TABLE 2

| Test compound shown by Example No. | $IC_{50}$ (M) |
|---|---|
| Example 1 | $9.63 \times 10^{-7}$ |
| Example 2 | $1.57 \times 10^{-7}$ |
| Example 3 | $1.74 \times 10^{-7}$ |
| Example 4 | $9.42 \times 10^{-7}$ |
| Example 6 | $6.81 \times 10^{-7}$ |
| Ozagrel HCl | $0.17 \times 10^{-7}$ |

All purine derivatives of the present invention shown in Examples 1–11 possess inhibitory effect against formation of $TXA_2$. Among compounds which exhibit potent inhibitory effect against lipid peroxidation shown in Table 2, compounds in Examples 2 and 3 were evaluated to exhibit remarkable inhibitory effect against formation of $TXA_2$. The inhibitory effect against formation of $TXA_2$ exhibited by the purine derivatives of the present invention is presumed to be caused by the inhibition of synthetic pathway of cyclic peroxide ($PGH_2$) in cyclooxygenase enzyme system or inhibition of $TXA_2$ synthesis from cyclic peroxide ($PGH_2$) with $TXA_2$ synthetase.

Test Example 3

(Prevention of adhesion of neutrophils to endothelial cells)
Inhibitory effect against adhesion of neutrophils to endothelial cells of the purine derivatives of the present invention was evaluated by the method shown below determining the preventive effect of adhesion of neutrophils to vascular endothelial cells.

In the present evaluation method, Fat peritoneal neutrophils were used as neutrophils and human umbilical vein endothelial cells were used as vascular endothelial cells. This evaluation was carried out according to the method described in Experimental Manuals for Bio-pharmaceutical Sciences Vol. 12, 'Inflammation and Allergy', Chapter 7, Neutrophils (Pub. by Hirokawa Publishing Co., Tokyo, Japan). The neutrophils were isolated, purified and subcultured in 199 medium. Then the neutrophils were labeled with $^{51}Cr$ and the neutrophil suspension was prepared to give a predetermined concentration of $3 \times 10^6$ cells/500 µl in 0.1% (w/v) BSA-199 medium. The endothelial cells of umbilical vein isolated from human specimen was available from a department of obstetrics and gynecology. The isolated pellets of endothelial cells were cultured in 20% FBS-199 medium.

Above mentioned vascular endothelial cells were cultured until confluent ($1.5 \times 10^5$ cells/well) and 500 µl of 0.1% (w/v) BSA-199 medium containing the test compound and thrombin, a neutrophil adhesion inducer, prepared before hand was added, then 500 µl of neutrophil suspension was immediately added and thoroughly dispersed. In the preceding experiment, the final concentration of thrombin was to be 1U/ml and the test compound was made 0.1% (v/v) DMSO solution. The test solution was stand cultured in an incubator in an atmosphere of 5% $CO_2$ at 37° C. for 20 min. After culture, the un-adhered neutrophils were suspended and removed by suction using a pipette. Then, 400 µl of 0.25% trypsin-0.01% EDTA solution was added and allowed to stand at 37° C. for 10 min., to separate the adhered neutrophils from the endothelial cells. The test solution was ice-cooled, 100µl of 199 medium containing 0.1% calf serum was added to terminate the trypsin reaction. Then, 400 µl of 0.1% NaOH solution was added. The separated neutrophils were transferred in a test tube for the determination of radioactivity and the total radioactivity of $^{51}Cr$ labeled neutrophils was determined. The adhesion index was calculated from the ratios between the radioactivity in 500 µl of the initial neutrophil suspension and those of after incubation. The inhibitory rate was calculated from the difference between the adhesion index determined for the reaction solution containing no test compound and those of solutions containing the test compound. When the difference of adhesion index was 0 (zero), then the inhibitory rate was made 0%, and when the adhesion index was equal to that without addition of inducer thrombin (blank group), then the inhibitory rate was made 100%.

Various final concentrations of the test compounds were selected to investigate the relationship between the final concentration and the inhibitory rate for the evaluation of inhibitory rate of neutrophil adhesion to vascular endothelial cells. Table 3 shows the results of the inhibitory rate for the final concentration at 10 µM.

TABLE 3

| Test compound shown by Example No. | Final concentration (µM) | Inhibitory rate (%) |
|---|---|---|
| Example 1 | 10 | 48 |
| Example 2 | 10 | 57 |
| Example 3 | 10 | 51 |
| Example 4 | 10 | 49 |
| Example 5 | 10 | 7 |
| Example 6 | 10 | 41 |

TABLE 3-continued

| Test compound shown by Example No. | Final concentration (μM) | Inhibitory rate (%) |
| --- | --- | --- |
| Example 7 | 10 | 26 |
| Example 8 | 10 | 31 |
| Example 9 | 10 | 28 |
| Example 10 | 10 | 28 |

Vascular endothelial cells were reported to enhance the adhesion of neutrophil by the stimulation with above-mentioned thrombin or histamine. In addition, drugs having PAF antagonistic activity were reported to inhibit the adhesion of neutrophils to endothelial cells caused by stimulation of thrombin or histamine. That is, since the purine derivatives of the present invention exhibit anti-PAF activity as shown in the following Test Example 4, these compounds suppressed the process of PAF dependent adhesion of neutrophils to endothelial cells.

Test Example 4

(Anti-PAF activity)

Anti-PAF activity of purine derivatives of the present invention was evaluated in the inhibition of platelet aggregation induced by PAF (platelet activation factor).

In the present evaluation, blood was drawn from rabbit and 9 volumes of the blood was added with 1 volume of 3.8% sodium citrate solution, centrifuged at 2,000 rpm for 3 min. to give platelet rich plasma (PRP). In a platelet aggregation determination apparatus, 200 μl of the PRP solution and 25 μl of a solution prepared from a predetermined amount of the test compound were mixed and incubated for 2 min. The incubated mixture was added with 25 μl of a solution containing a predetermined amount of PAF to cause platelet aggregation induced by PAF in the test solution. A concentration of PAF was 10 nM in the test solution. The inhibitory rate against platelet aggregation induced by PAF was calculated from the changes of transmission accompanied by the platelet aggregation. When the test solution containing the test compound showed same transmission change with that of containing no test compound (blank group), then the inhibitory rate was made 0%, and when there was no changes in transmission, then the inhibitory rate was made 100%.

Various concentrations of the test compounds in the test solution were selected to investigate the relationship between the concentration and the inhibitory rate for the evaluation of inhibitory rate of platelet aggregation induced by PAF. Table 4 shows the results of the inhibitory rate for the concentration at 30 μM. The inhibitory rate for the positive control compound, CV-3988 (rac-3-(N-n-octadecyl-carbamoyl)-2-methoxypropyl-2-thiazolium ethyl phosphate) is also shown in Table 4. CV-3988 is an analogue of PAF and was reported to exhibit high anti-PAF activity (see Life Science, 32, 1975–1982 (1983)).

TABLE 4

| Test compound shown by Example No. | Concentration (μM) | Inhibitory rate (%) |
| --- | --- | --- |
| Example 1 | 30 | 46 |
| Example 2 | 30 | 57 |
| Example 3 | 30 | 78 |
| Example 4 | 30 | 61 |

TABLE 4-continued

| Test compound shown by Example No. | Concentration (μM) | Inhibitory rate (%) |
| --- | --- | --- |
| Example 5 | 30 | 15 |
| Example 6 | 30 | 35 |
| Example 7 | 30 | 5 |
| Example 8 | 30 | 5 |
| Example 9 | 30 | 2 |
| Example 10 | 30 | 4 |
| Example 11 | 30 | 53 |
| CV-3988 | 30 | 78 |

Among purine derivatives of the present invention shown in Examples 1–11, compounds prepared by Examples 1–4 and 11 exhibited marked inhibitory effect as shown in Table 4. The inhibitory effect against PAF induced platelet aggregation was presumed to be caused by as potent anti-PAF activity as that of positive control compound CV-3988.

Test Example 5

(Activity for the endotoxin induced death) Activity of purine derivatives of the present invention for endothelial cell damage by endotoxin was evaluated by the following method.

In the present method of evaluation, endotoxin caused endothelial cell damage was induced by intraperitoneal administration of LPS (E. coli 055:B5) to male ICR mice. The body weight of test mice was determined beforehand and a dose of 15 mg/kg (body weight) of LPS was predetermined. After administration of LPS, the difference between the number of dead mice induced by endotoxin within 4 days and the total number of mice was divided by the total number of mice to give the survival rate. The dose per body weight of test compound was predetermined and orally administered at 30 min. before induction (LPS administration) and at 8 hrs. after the induction, twice in total. The test compounds were suspended in 0.5% CMC—Na aqueous solution.

Various doses of the test compounds per body weight were selected to investigate the relationship between the dose and survival rate for the evaluation of inhibitory effect against endotoxin induced death. Table 5 shows the results of compound prepared in Example 2. While, control group was given the same dose of 0.5% CMC—Na aqueous solution only. An increase in survival rate with the increase of dose was clearly observed. That is, the inhibitory effect of the compound of the present invention against endotoxin induced death was clearly observed.

TABLE 5

| Group | Dose (mg/kg) | Survival rate (%) |
| --- | --- | --- |
| (Control) | (0) | 50 |
| Compound of | 100 | 68 |
| Example 2 | 300 | 75 |

In addition, endothelial cell damage due to endotoxin at first occurs in the activation of complement and the resultant $C5_a$ induces the activation of phagocytes such as neutrophils and macrophages. These phagocytes produce active oxygen and PAF, which causes the damages to endothelial cells. Furthermore, tumor necrosis factor (TNF) derived from activated macrophage induces the production of active oxygen from neutrophils and aggravates the damages of cells. While, it is reported that active oxygen itself induces the expression of cellular adhesive molecule and $H_2O_2$ derived from active oxygen induces the synthesis of PAF in endothelial cells to cause PAF dependent adhesion of neutrophils to endothelial cells. In addition, it is repeated that the adhesion of neutrophils to endothelial cells increased the active oxygen productivity from neutrophils, and also that $C5_a$ generation was accelerated by $H_2O_2$ derived from active oxygen. As explained above, endotoxin induced damages of endothelial cells causes interactions of above-mentioned various organs and mechanisms and increases the inflammatory responses. The purine derivatives of the present invention reduces the active oxygen by their activity of scavenging active oxygen. Their adhesion preventing activity inhibits the initial process of cellular damages, and ameliorates or prevents the aggravation of endotoxin induced damages of endothelial cells. The evaluated results in the present invention against endotoxin induced death reflect above-mentioned preventive effects.

Test Example 6

(Effect on nephrotoxin-induced nephritis)

Inhibitory effect of purine derivatives of the present invention against nephrotoxin-induced nephritis was evaluated by the following method.

In the present method of evaluation, nephrotoxin-induced nephritis was induced by administration of anti-GBM (glomerular basement membrane) serum to 9-week old male SD rats. The anti-GBM serum was prepared according to a known method (see Kidney and Dialysis (Jin to Toseki) 31, Special Issue, p. 202–206 (1991), Pub. by Tokyo Igakusha Ltd., Tokyo, Japan). Anti-GBM serum was intravenously administered at an induction dose of 0.15 ml/300 g (body weight). The predetermined dose per body weight of the test compound was suspended in 0.5% CMC—Na aqueous solution and orally administered once daily for consecutive 7 days starting from one day before induction (administration of anti-GBM serum). While, control group was given the same dose of 0.5% CMC—Na aqueous solution only. During the administration period of the test compound, urinary protein was measured every 24 hrs. Seven days after the induction, blood was drawn to prepare serum sample by a conventional method, and BUN, total cholesterol and triglyceride were measured.

Various doses of the test compounds per body weight were selected to investigate the relationship between the dose and urinary protein for the evaluation of inhibitory effect against nephrotoxin-induced nephritis. Table 6 shows the results of compound prepared by Example 2. Comparison with that of the control group (administration only 0.5% CMC—Na) clearly demonstrated the dose dependent inhibitory effect against increase of urinary protein indicating dose dependent inhibition against nephrotoxin-induced nephritis. Furthermore, Table 7 shows the concentrations of serum BUN, total cholesterol and triglyceride at day 7 after the induction. Comparison of these concentrations with those of the control group showed dose dependent decrease. The inhibitory effect against nephrotoxin-induced nephritis was observed with dose-dependent manner.

TABLE 6

| | | Urinary protein | | |
| Group | Dose (mg/kg) | One day before induction | Day 3 after induction | Day 5 after induction |
| --- | --- | --- | --- | --- |
| (Control) | (0) | 12.2 ± 1.1 | 74.1 ± 25.6 | 72.1 ± 25.7 |
| Compound of | 30 | 10.5 ± 0.8 | 49.0 ± 16.7 | 52.8 ± 16.7 |
| Example 2 | 100 | 12.2 ± 2.5 | 14.5 ± 1.7* | 14.3 ± 1.0* |

Values indicated means ± S.E. and unit indicates mg/day
*p < 0.05

TABLE 7

| | | Serum parameter | | |
| Group | Dose (mg/kg) | BUN | Total cholesterol | triglyceride |
| --- | --- | --- | --- | --- |
| (Control) | (0) | 27.6 ± 0.9 | 75 ± 3 | 161 ± 25 |
| Compound of | 30 | 26.9 ± 0.8 | 72 ± 6 | 125 ± 20 |
| Example 2 | 100 | 23.6 ± 1.6* | 66 ± 2* | 60 ± 4** |

Values indicate means ± S.E. and unit indicates mg/dl
*p < 0.05,
**p < 0.01

In nephrotoxin-induced nephritis of the present Test Example, damage of renal tissue, particularly glomerular tissue is induced by immunological mechanism by the administration of anti-GBM serum. In addition, deposition of immune complex, or activation of complement by the binding also induced activation of leukocytes and resulted in the aggravation of tissue damage due to active oxygen produced by glomerular endothelial cells, mesangial cells or leukocytes. These mechanisms interact with each other to amplify the inflammation responses. Above-mentioned effective inhibition of nephrotoxin-induced nephritis reflects the preventive effects on lipid peroxidation, $TXA_2$ synthesis and adhesion of neutrophils, and anti-PAF action of the purine derivatives of the present invention.

As clarified and proved in the above Test Examples, the purine derivatives of the present invention exhibit preventive effects against lipid peroxidation, $TXA_2$ synthesis, adhesion of neutrophils, anti-PAF activity, endotoxin induced death and nephrotoxin-induced nephritis.

From the biological activities of the purine derivatives of the present invention, the following activities can be predicted. Activated leukocytes (neutrophils) produce proteases such which as elastase, which are inhibited by proteins such as protease inhibitor in the tissue and blood. Methionine is an active center of $\alpha_1$-antitrypsin which belongs to one of those proteins. However, that methionine is oxidatively inactivated by HOCl produced from $H_2O_2$ and Cl⁻ in the presence of myeloperoxidase (MPO) in azure granules of neutrophil and results in the aggravation of tissue damage with proteases such as elastase. The purine derivatives of the present invention have action of scavenging active oxygen and inhibit the process of oxidative damage of proteins (protease inhibitor) such as $\alpha_1$-antitrypsin and will inhibit the onset and aggravation of tissue damages caused by protease. Furthermore, the inhibitory or antagonistic activity against proteases produced by these leukocytes such as neutrophils will also inhibit the processes of extracellular substrate lyric action of leukocyte with protease and infiltration out of blood vessel into tissues. In addition, the purine derivatives of the present invention will inhibit the elevation of cellular Ca level in vascular endothelial cells by elastase derived from leukocytes, which leads to the cell contraction reaction, changes of cell forms and elevation of vascular permeability.

As described above, it is clear that the purine derivatives of the present invention scavenge the active oxygen which directly relates to the induction of tissue damages. Furthermore, inhibitory activity against elevation of vascular permeability and inhibition of infiltration of leukocytes into inflammatory tissues are expected. In addition, the purine derivatives of the present invention highly inhibit the adhesion of leukocytes to endothelial cells which initiates the tissue damages and prevent the onset or aggravation of inflammatory responses.

Example of pharmaceutical preparation

An example for the production of an oral pharmaceutical preparation using a purine derivative of the present invention is shown below. Tablets having the composition shown in Table 8 below were prepared by a conventional method using pulverized compound prepared in Example 2 and pharmacologically acceptable excipients.

TABLE 8

|  | Content/tablet |
| --- | --- |
| Compound of Example 2 | 100 mg |
| Lactose | 100 mg |
| Potato starch | 30 mg |
| Hydroxypropylcellulose | 5 mg |
| Magnesium stearate | 5 mg |

As described above, the purine derivatives of the present invention exhibit the above-mentioned biological activities. The pharmaceutical preparations containing the purine derivatives or pharmacologically acceptable salts thereof of the present invention exhibit the inhibition of inflammatory responses caused by the mediators such as active oxygen or $TXA_2$ released from activated leukocytes (neutrophils), and inhibit the aggravation of inflammatory responses due to activated leukocytes (neutrophils) caused by adhesion of leukocytes (neutrophils and eosinophils) to endothelial cells. That is, purine derivatives of the present invention prevent the tissue damages caused by mediators such as active oxygen and $TXA_2$ in the initial stage of inflammation. In addition, purine derivatives of the present invention prevent the aggravation of inflammatory responses accompanied with the adhesion of activated leukocytes to cells in the lesion. Thus, they exhibit advantages in the efficacy as anti-inflammatory drugs in all stages of inflammatory diseases caused by leukocytes.

We claim:

1. A purine derivative shown by formula (I):

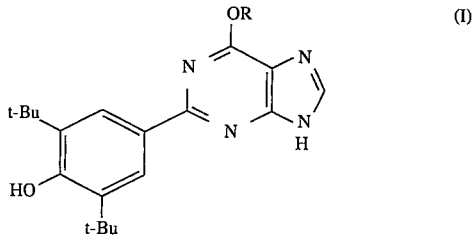

wherein,

R is selected from the group consisting of H atom, a straight chain alkyl group having 1–10 carbon atoms, a branched chain alkyl group having 3–10 carbon atoms, an alkyl group having 1–10 carbon atoms substituted with one carboxyl group, 4-carboxybenzyl group and phenethyl group;

or pharmacologically acceptable salt thereof.

2. A composition for the inhibition of inflammatory diseases comprising:

a purine derivative according to claim 4; and a pharmacologically acceptable excipient.

3. The composition of claim 2 wherein the purine derivative is 2-(3,5-di-tert-butyl-4-hydroxyphenyl)-6-n-propoxypurine or a pharmacologically acceptable salt thereof.

4. The composition of claim 2 wherein the purine derivative is 6-n-butoxy-2-(3,5-di-tert-butyl-4-hydroxyphenyl)purine or a pharmacologically acceptable salt thereof.

5. The composition of claim 2 wherein the purine derivative is 2-(3,5-di-tert-butyl-4-hydroxyphenyl)-6-phencthyloxypurine or a pharmacologically acceptable salt thereof.

* * * * *